(12) United States Patent
Chang et al.

(10) Patent No.: US 6,426,500 B1
(45) Date of Patent: Jul. 30, 2002

(54) METHOD FOR PROTECTING A SPECIFIC REGION IN A SAMPLE APPLIED IN PREPARING AN ULTRA-THIN SPECIMEN

(75) Inventors: Wen-Tung Chang; Mei-Jung Lu, both of Hsinchu (TW)

(73) Assignee: Mosel Vitelic Inc., Hsinchu (TW)

( * ) Notice: Subject to any disclaimer, the term of this patent is extended or adjusted under 35 U.S.C. 154(b) by 0 days.

(21) Appl. No.: 09/430,895

(22) Filed: Nov. 1, 1999

(30) Foreign Application Priority Data

Nov. 2, 1998 (TW) ........................................ 87118217 A

(51) Int. Cl.$^7$ ................................................. G01N 1/32
(52) U.S. Cl. ........................................ 250/307; 250/309
(58) Field of Search ................................. 250/307, 309; 216/38, 39; 204/192, 34

(56) References Cited

U.S. PATENT DOCUMENTS 5,116,771 A * 5/1992 Karulkar ...................... 437/40
5,369,058 A * 11/1994 Burns et al. ................. 437/209
5,990,478 A * 11/1999 Liu ............................. 250/307

* cited by examiner

*Primary Examiner*—John R. Lee
*Assistant Examiner*—Anthony Quash
(74) *Attorney, Agent, or Firm*—Peter F. Corless; Steven M. Jensen; Edwards & Angell, LLP

(57) ABSTRACT

A method for protecting a specific region in the sample applied in preparing an ultra-thin specimen is disclosed. The method includes the steps of (a) forming a first concavity on a first side of the specific region by a focus ion beam (FIB) technique, (b) forming a second concavity on a second side of the specific region opposite to the first side by the focus ion beam technique, (c) filling the first concavity and the second concavity with a first metallic packing and a second metallic packing respectively, and (d) forming a third metallic packing on the specific region and extending to connecting with the first metallic packing and the second metallic packing to define a protecting device for protecting the specific region.

19 Claims, 3 Drawing Sheets

METHOD FOR PROTECTING A SPECIFIC REGION IN A SAMPLE APPLIED IN PREPARING AN ULTRA-THIN SPECIMEN

FIELD OF THE INVENTION

The present invention is related to a method for protecting a specific region applied in preparing a specimen, and more particularly to a method for protecting a specific region in a sample applied in preparing an ultra thin specimen to be observed by a microscope.

BACKGROUND OF THE INVENTION

Nowadays, due to the improvement in the manufacturing process of the microelectronic element and tendency of demanding a smaller line width, the semiconductor analysis is getting more and more difficult, particularly in the analysis technology of the finished dynamic random access memory (DRAM) having a size less than 0.25 $\mu$m.

In the semiconductor industry, it is common to use a scanning electron microscope (SEM) to observe the surface condition of a wafer and use a transmission electron microscope (TEM) to examine the microstructure of a wafer to ensure that the fabricated microelectronic elements satisfy an expected standard. However, because the resolution of the scanning electron microscope (SEM) is not good enough to observe the detailed structure of the microelectronic elements, it is replaced by the transmission electron microscope (TEM) to make major failure analysis. As one may realize, most of the problems in TEM application are related to sample preparation, which is the most difficult part of TEM analysis. Traditionally, a sample is cut from a wafer to be examined. After thoroughly polished, the sample becomes ultra-thin and is ready to be examined by the transmission electron microscope (TEM) for determining the quality of the wafer. However, during the preparing process, an optical microscope and a laser mark must be employed so that an ultra-thin specimen for fixed-point failure analysis can be prepared easily.

At the present time, a conventional method for marking a specific region in a sample utilizes a laser technique. However, there are some defects by utilizing the laser technique to make the marks.

(1) The laser cannot be focused further so that the width of the mark made by the laser technique is many times than 0.25 $\mu$m. In addition, due to the resolution limitation of the optical microscope, a single-bit failure analysis which has a size less than 0.35 $\mu$m cannot be carried out by employing the laser technique to prepare the specimen.

(2) The laser technique utilizes a laser light beam having a high energy to remove the material in a mark region of the sample so as to form a concavity to be observed by microscopy. However, due to the damage of the high-energy laser light beam, a plurality of cracks are formed on the periphery of the concavity. When the sample is milled and/or polished to make an ultra-thin TEM specimen, those cracks may be propagated due to the local stress to form additional defects in the TEM specimen, which may seriously influence the analysis result of the microelectronic element.

A focus ion beam technique (FIB) was designed to make TEM sample instead of the laser technique. The focus ion beam (FIB) technique utilizes focused high-energy gallium ions to remove materials from both sides of the desired region. The focus ion beam (FIB) technique can offer a reliable method to precisely obtain a cross section of the specific area, and the sample can be thinned to less than 0.1 $\mu$m. However, this method requires very expensive equipment and cost for preparing an ultra-thin specimen, which further limits the usage of this method. Therefore, it is not worthy to prepare an ultra-thin specimen directly by the focus ion beam (FIB) technique.

For the above reason, it is desirable to develop a low-cost and effective method for protecting a specific region in the sample applied in preparing an ultra-thin specimen of 0.25 $\mu$m or less size dynamic random access memory (DRAM).

SUMMARY OF THE INVENTION

It is therefore a primary object of the present invention to provide an effective method for protecting a specific region in a sample applied in prepared an ultra-thin specimen to be observed by a microscope.

Another object of the present invention is to provide a protecting device formed on the sample for protecting a specific region to be milled and polished during the preparing process so that the sample can be polished to a required thickness without any damage.

It is further an object of the present invention to provide an effective method for protecting a specific region in a sample so as to avoid necessary damage for the ultra-thin specimen and reduce the preparing cost for the ultra-thin specimen.

In order to accomplish the object of the present invention, a method for protecting a specific region in a sample applied in preparing an ultra-thin specimen is provided. The method includes the steps of (a) forming a first concavity on a first side of the specific region by a focus ion beam (FIB) technique, (b) forming a second concavity on a second side of the specific region opposite to the first side by focus ion beam technique, (c) filling the first concavity and the second concavity with a first metallic packing and a second metallic packing respectively, and (d) forming a third metallic packing over the specific region, the first metallic packing and the second metallic packing to define a protecting device for protecting the specific region.

In accordance with one aspect of the present invention, the third metallic packing has a first end connecting with the first metallic packing and a second end connecting with the second metallic packing to form the protecting device.

Preferably, the third metallic packing has a first end protruding beyond the first metallic packing and a second end connecting with the second metallic packing to form the protecting device. More preferably, the third metallic packing has a first end protruding beyond the first metallic packing and a second end protruding beyond the second metallic packing to form the protecting device.

In accordance with another aspect of the present invention, after the step (c), the method further includes a step of forming a third concavity on the first side of the specific region adjacent to the first concavity and then filling the third concavity with a fourth metallic packing. Preferably, the third metallic packing is extending to connect with the first, the second and the fourth metallic packing to form the protecting device.

Preferably, after the step (d), the method further includes a step of (d1) forming a fourth concavity on a third side of the specific region. More preferably, after the step (d1), the method further includes a step of (d2) forming a fifth concavity on a fourth side of the specific region opposite to the third side.

In accordance with another aspect of the present invention, after the step (d), the method further includes a step of (e) polishing one side of the sample with a higher polishing rate till the protecting device is partially polished.

In accordance with another aspect of the present invention, after the step (e), the method further includes a step of (f) polishing said side of the sample with a lower polishing rate till the protecting device is completely exposed.

In accordance with another aspect of the present invention, after the step (f), the method further includes a step of (g) stopping polishing said one side of the sample and then polishing the other side of the sample opposite to said one side.

Preferably, the step (c) is executed by a sputtering technique.

Preferably, the microscope is one selected from the group consisting of an optical microscope (OM), a transmission electron microscope (TEM), and a scanning electron microscope (SEM)

Preferably, each of the concavities is substantially a parallelepiped having a length and width ranged from 1 to 1.5 $\mu$m and a depth ranged from 2 to 3 $\mu$m.

Preferably, each of the metallic packings is made of one selected from Platinum (Pt) and Tungsten (W).

Preferably, the distance between the first concavity and the second concavity is about 5 $\mu$m.

Preferably, the ultra-thin specimen has a thickness of about 0.2 $\mu$m.

Preferably, the specific region has a length of about 5 $\mu$m and a width of about 0.2 $\mu$m.

It is further another object of the present invention to provide a method for protecting a specific region in a sample. The method is applied in preparing an ultra-thin specimen to be observed by a microscope. The method include the steps of (a) forming a first concavity on a first side of the specific region by a focus ion beam (FIB) technique, (b) forming a second concavity on a second side of the specific region opposite to the first side by the focus ion beam technique, (c) filling the first concavity and the second concavity with a first metallic packing and a second metallic packing respectively, and (d) forming a third metallic packing on the specific region, wherein the third metallic packing has a first end surface connecting with an inner surface of the first metallic packing and a second end surface connecting with an inner surface of the second metallic packing to define a protecting device for protecting the specific region.

The present invention may best be understood through the following description with reference to the accompanying drawings, in which:

DETAILED DESCRIPTION OF THE PREFERRED EMBODIMENTS

In order to ensure that the fabricated microelectronic elements satisfy an expected standard, a fixed-point failure analysis of the microelectronic element must be carried out by TEM microscopy. The method of the present invention is provided for protecting an analyzed target in a sample applied in preparing an ultra-thin specimen to be observed by a microscope.

The method of the present invention includes following steps. Firstly, a first concavity 12 is formed on a first side of the specific region 11 in the sample 10 by a force ion beam technique. Secondly, a second concavity 13 is formed on a second side of the specific region 11 opposite to the first side by the force ion beam technique. Then, a first metallic packing and a second metallic packing are sputtered in the first concavity 12 and the second concavity 13 respectively. Finally, a third metallic packing is formed over the specific region 11 and extending to connect with the first metallic packing and the second metallic packing to form a protecting device for protecting the specific region 11 during a preparing process. The protecting device can protect the specific region 11 which includes the analyzed target during a milling and/or polishing process.

Figure 1:
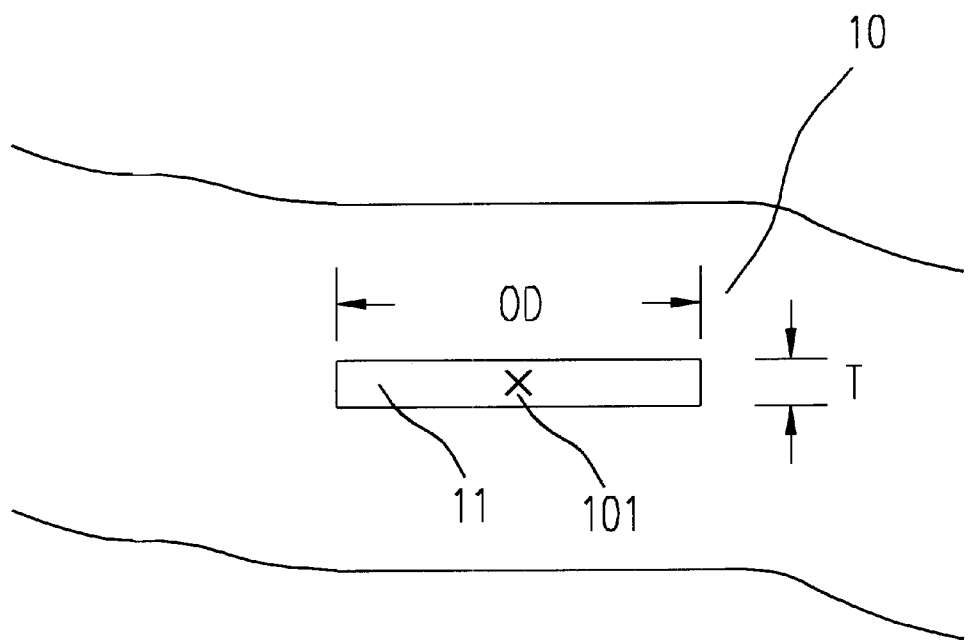
FIG. 1 is a plane view showing a protected specific region in the sample.
Figure 2:
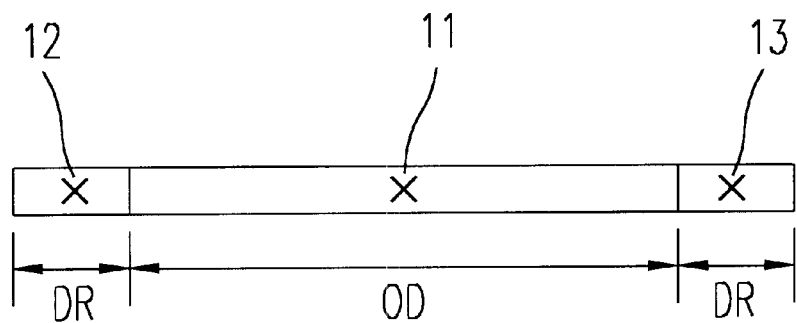
FIG. 2 is a plane view of the sample showing a first preferred embodiment of the present invention.

Please refer to FIG. 1 showing a plane view of the protected specific region 11 in the sample 10. The specific region 11 has a length (OD) of about 5 $\mu$m and a width (T) of about 0.2 $\mu$m. Certainly, a fixed point 101 which represents the analyzed target is positioned in the central part of the specific region 11. Please refer to FIG. 2 showing the first embodiment of the present invention. The first concavity 12 and the second concavity 13 are respectively formed on two opposite sides of the specific region 11. Preferably, the distance between the first concavity 12 and the second concavity 13 is about 5 $\mu$m. Each of the concavities (12 and 13) is substantially a parallelepiped having a length (DR) and width ranged from 1 to 1.5 $\mu$m and a depth ranged from 2 to 3 $\mu$m. Certainly, the depths of those concavities (12 and 13) depend on the depth of the device.

Figure 3:
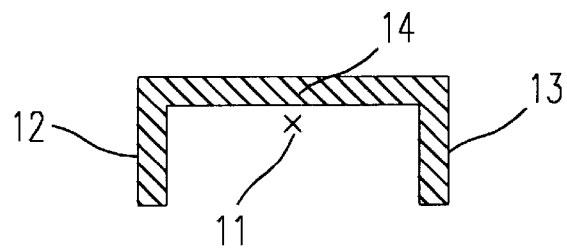
FIG. 3 is a cross-sectional view of FIG. 2.
Figure 4:
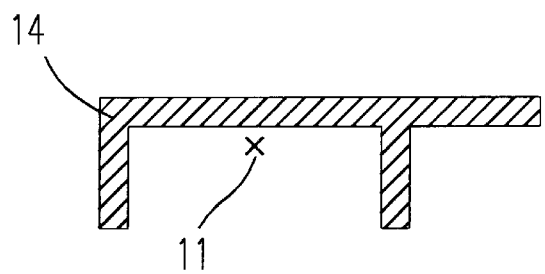
FIG. 4 is a cross-sectional view of the sample showing a second preferred embodiment of the present invention.
Figure 5:
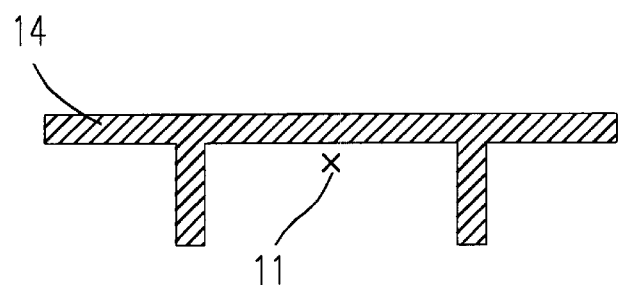
FIG. 5 is a cross-sectional view of the sample showing a third preferred embodiment of the present invention.

Please refer to FIG. 3 showing a cross-sectional view of the sample 10 according to the first embodiment of the present invention. As shown in FIG. 3, the first metallic packing is sputtered in the first concavity 12 and the second metallic packing is sputtered in the second concavity 13. A third metallic 14 is formed over the specific region 11, and has a first end and a second end connecting with the first metallic packing and the second metallic packing respectively to form the protecting device. The protecting device can protect the analyzed target 101 from damage during a preparing process. Preferably, each of the metallic packing is made of one selected from Platinum (Pt) and Tungsten (W). However, the shape of the protecting device is not limited. Please refer to FIG. 4 showing a second embodiment of the present invention. Preferably, the third metallic packing 14 has a first end protruding beyond the first metallic packing and a second end connecting with the second metallic packing to form the protecting device. Please refer to FIG. 5 showing a third embodiment of the present invention. More preferably, the third metallic packing 14 has a first end protruding beyond the first metallic packing and a second end protruding beyond the second metallic packing to form the protecting device. Those embodiments have proven to be effective to prevent the formation of cracks in analyzed target during the milling and/or polishing process.

Figure 6:
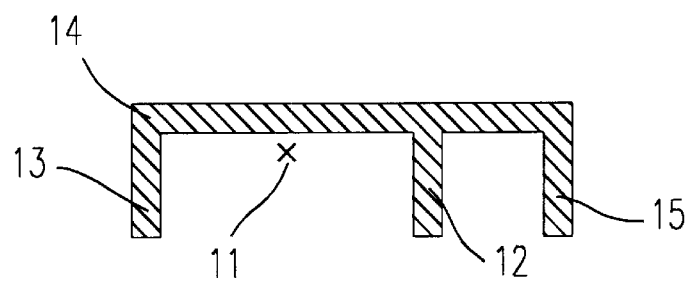
FIG. 6 is a cross-sectional view of the sample showing a fourth preferred embodiment of the present invention.
Figure 7:
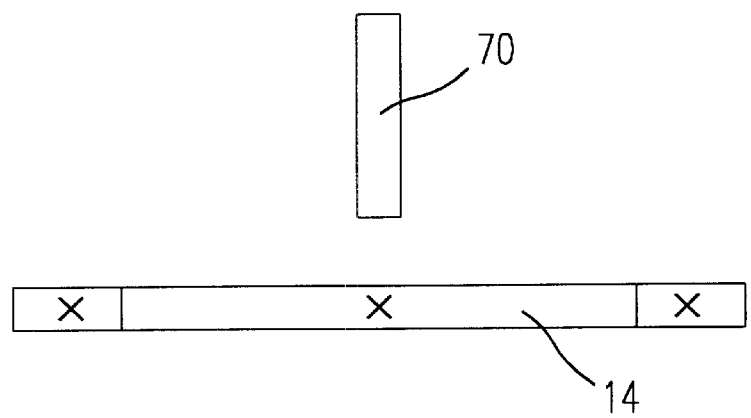
FIG. 7 is a plane view showing a fourth concavity formed on the third side of the specific region.
Figure 8:
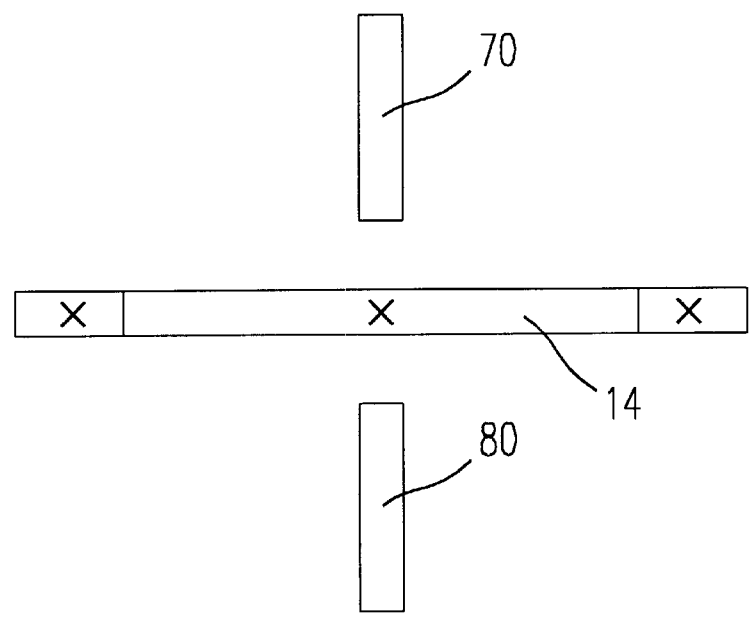
FIG. 8 is a plane view showing a fifth concavity formed on the fourth side of the sample.

Please refer to FIG. 6 showing a fourth embodiment of the present invention. As shown in FIG. 6, a third concavity 15 can be further formed on the first side of the specific region 11 adjacent to the first concavity 12 and sputtered with a fourth metallic packing. Then, the third metallic packing 14 is formed over the specific region and extending to connect with the first, the second and the fourth metallic packing to form the protecting device.

After forming a protecting device on the specific region 11 in the sample 10, a milling technique is used to mill one side of the sample. When the operator observes that the side of the sample is close to the protecting device, the milling process must be stopped and a polishing process must be executed continuously. During the polishing process, the side of the sample 10 can be polished at a higher polishing rate till the protecting device is partially polished. Then, the side of the sample can be polished at a lower polishing rate till the protecting device is completely exposed. After polishing the one side of the sample, the other side of the sample opposite to the one side can also be milled and polished in the same steps. As a result of the polishing process, the sample 10 become an ultra-thin specimen having a thickness of about 0.2 $\mu$m which is suitable for the application of the TEM. Certainly, if possible, the thickness of the specimen can be reduced to less than 0.2 $\mu$m so as to make the fixed-point failure analysis more effective.

In addition, during the polishing process, the sample must be observed by an optical microscope. Certainly, the microscope can be one of the optical microscope (DM), the transmission electron microscope (TEM), or the scanning electron microscope (SEM). Generally, the resolution of the optical microscope in top view is about 0.2~0.5 $\mu$m. If the metallic packing can not be easily observed by the optical microscope in top view during the polishing process, a fourth concavity 70 can be formed on the third side of the specific region 11 so that the metallic packing 14 can be observed easily. Preferably, a fifth concavity 80 is formed on the fourth side of the specific region 11 opposite to the third side.

According to the description with reference to the accompanying drawings, the method of the present invention can improve the defects encountered in the prior art. In addition, the method of the present invention can protect tile sample and avoid unnecessary damage for the analyzed target of an ultra-thin specimen during the preparing process. Moreover, the method of the present invention not only overcomes the difficulty in the failure analysis of the finished DRAM having a size less than 0.25 $\mu$m, but also reduces the cost for preparing an ultra-thin specimen.

The above embodiments can be modified by any skillful person in the art without departing the spirit and scope of the accompanying claims.

What is claim is:

1. A method for protecting a specific region in a sample applied in preparing an ultra-thin specimen to be observed by a microscope, comprising steps of:
    (a) forming a first parallelepiped-like concavity on a first side of said specific region by a focus ion beam (FIB) technique;
    (b) forming a second parallelepiped-like concavity on a second side of said specific region opposite to said first side by said focus ion beam technique;
    (c) filling said first concavity and said second concavity with a first metallic packing and a second metallic packing respectively; and
    (d) forming a third metallic packing over said specific region, said first metallic packing and said second metallic packing directly to define a protecting device for protecting said specific region.

2. The method according to claim 1 wherein said third metallic packing has a first end connecting with said first metallic packing and a second end connecting with said second metallic packing to form said protecting device.

3. The method according to claim 1 wherein said third metallic packing has a first end protruding beyond said first metallic packing and a second end connecting with said second metallic packing to form said protecting device.

4. The method according to claim 1 wherein said third metallic packing has a first end protruding beyond said first metallic packing and a second end protruding beyond said second metallic packing to form said protecting device.

5. The method according to claim 1 wherein said step (c) is executed by a sputtering technique.

6. The method according to claim 1 wherein said microscope is one selected from the group consisting of an optical microscope (OM), a transmission electron microscope (TEM), and a scanning electron microscope (SEM).

7. The method according to claim 1 wherein each of said concavities has a length and width ranging from 1 to 1.5 $\mu$m and a depth ranging from 2 to 3 $\mu$m.

8. The method according to claim 1 wherein each of said metallic packings is made of one selected from Platinum (Pt) and Tungsten (W).

9. The method according to claim 1 wherein the distance between said first concavity and said second concavity is about 5 $\mu$m.

10. The method according to claim 1 wherein said ultra-thin specimen has a thickness of about 0.2 $\mu$m.

11. The method according to claim 1 wherein said specific region has a length of about 5 $\mu$m and a width of about 0.2 $\mu$m.

12. The method according to claim 1 wherein after said step (c), said method further includes a step of forming a third concavity on said first side of said specific region adjacent to said first concavity and then filling said third concavity with a fourth metallic packing.

13. The method according to claim 5 wherein said third metallic packing is extending to connect with said first, said second and said fourth metallic packing to form said protecting device.

14. The method according to claim 1 wherein after said step (d), said method further includes a step of (d1) forming a fourth concavity on a third side of said specific region.

15. The method according to claim 7 wherein after said step (d1), said method further includes a step of (d2) forming a fifth concavity on a fourth side of said specific region opposite to said third side.

16. The method according to claim 1 wherein after said step (d), said method further includes a step of (e) polishing one side of said sample with a higher polishing rate till said protecting device is partially polished.

17. The method according to claim 9 wherein after said step (e), said method further includes a step of (f) polishing said one side of said sample with a lower polishing rate till said protecting device is completely exposed.

18. The method according to claim 10 wherein after said step (f), said method further includes a step of (g) stopping polishing said one side of said sample and then polishing the other side of said sample opposite to said one side.

19. A method for protecting a specific region in a sample applied in preparing an ultra-thin specimen to be observed by a microscope, comprising steps of:

(a) forming a first parallelepiped-like concavity on a first side of said specific region by a focus ion beam (FIB) technique;
(b) forming a second parallelepiped-like concavity on a second side of said specific region opposite to said first side by said focus ion beam technique;
(c) filling said first concavity and said second concavity with a first metallic packing and a second metallic packing respectively; and
(d) forming a third metallic packing on said specific region directly, wherein said third metallic packing has a first end surface connecting with an inner surface of said first metallic packing and a second end surface connecting with an inner surface of said second metallic packing to define a protecting device for protecting said specific region.

* * * * *